(12) United States Patent
House

(10) Patent No.: US 8,888,747 B2
(45) Date of Patent: Nov. 18, 2014

(54) CATHETER ASSEMBLY WITH VENTS

(75) Inventor: Jamie Glen House, Colorado Springs, CO (US)

(73) Assignee: Adapta Medical, Inc., Colorado Springs, CO (US)

( * ) Notice: Subject to any disclaimer, the term of this patent is extended or adjusted under 35 U.S.C. 154(b) by 1101 days.

(21) Appl. No.: 11/546,339

(22) Filed: Oct. 12, 2006

(65) Prior Publication Data

US 2008/0091136 A1     Apr. 17, 2008

(51) Int. Cl.
| | | |
|---|---|---|
| *A61M 3/00* | (2006.01) | |
| *A61M 5/00* | (2006.01) | |
| *A61M 27/00* | (2006.01) | |
| *A61M 25/01* | (2006.01) | |
| A61M 25/00 | (2006.01) | |
| A61M 25/06 | (2006.01) | |

(52) U.S. Cl.
CPC ........... *A61M 25/01* (2013.01); *A61M 25/0017* (2013.01); *A61M 25/002* (2013.01); *A61M 2025/0681* (2013.01)
USPC .............................. 604/171; 604/45; 604/544

(58) Field of Classification Search
CPC ................. A61M 25/0111; A61M 2210/1085; A61M 2210/1096; A61M 2210/1078; A61F 2/042
USPC ...................... 604/45, 171, 544, 523, 23, 349
See application file for complete search history.

(56) References Cited

U.S. PATENT DOCUMENTS

| | | | | |
|---|---|---|---|---|
| 2,937,643 | A * | 5/1960 | Elliot ............................ | 604/163 |
| 3,835,857 | A * | 9/1974 | Rogers et al. ................. | 604/349 |
| 3,937,220 | A * | 2/1976 | Coyne ........................... | 604/119 |
| 4,168,699 | A * | 9/1979 | Hauser ........................... | 600/581 |
| 4,178,735 | A * | 12/1979 | Jackson ......................... | 53/473 |
| 4,204,527 | A * | 5/1980 | Wu et al. ........................ | 600/575 |
| 4,327,723 | A * | 5/1982 | Frankhouser ................. | 604/171 |
| 4,327,735 | A * | 5/1982 | Hampson ....................... | 604/171 |
| 4,622,033 | A | 11/1986 | Taniguchi | |
| 4,723,955 | A * | 2/1988 | Vaillancourt ................. | 604/405 |
| 4,743,243 | A * | 5/1988 | Vaillancourt ................. | 604/405 |
| 4,772,275 | A | 9/1988 | Erlich | |
| 4,834,710 | A | 5/1989 | Fleck | |
| 4,957,487 | A * | 9/1990 | Gerow .......................... | 604/133 |
| 5,125,902 | A * | 6/1992 | Berry et al. .............. | 604/170.03 |
| 5,149,326 | A | 9/1992 | Woodgrift et al. | |
| 5,181,913 | A | 1/1993 | Erlich | |
| 5,228,851 | A * | 7/1993 | Burton .......................... | 433/116 |
| 5,234,411 | A * | 8/1993 | Vaillancourt ................. | 604/171 |
| 5,300,022 | A * | 4/1994 | Klapper et al. ................. | 604/35 |
| 5,306,241 | A * | 4/1994 | Samples ....................... | 604/544 |
| 5,314,409 | A * | 5/1994 | Sarosiek et al. ......... | 604/101.03 |
| 5,349,950 | A * | 9/1994 | Ulrich et al. ............. | 128/207.16 |
| 5,417,664 | A * | 5/1995 | Felix et al. .................... | 604/129 |
| 5,715,815 | A * | 2/1998 | Lorenzen et al. ........ | 128/207.14 |
| 5,779,670 | A | 7/1998 | Bidwell et al. | |

(Continued)

*Primary Examiner* — Aarti B Berdichevsky
*Assistant Examiner* — Bradley Osinski
(74) *Attorney, Agent, or Firm* — Moazzam & Associates, LLC

(57) ABSTRACT

A catheterization device with vents is disclosed which serves to prevent a build-up of air pressure within a closed protective sheath. The vents may be in the form of small openings and may be situated at the distal portion of the catheterization device. The small openings may optionally be covered. They may be on the protective sheath itself or they may be on a distal terminus body connected to the protective sheath. Sample openings include an attached valve which connects the inside of the protective sheath with the external environment, a gas permeable membrane, or a slitted membrane forming 4 flaps.

20 Claims, 4 Drawing Sheets

(56) References Cited

U.S. PATENT DOCUMENTS

| | | |
|---|---|---|
| 5,792,114 A | 8/1998 | Fiore |
| 5,800,409 A * | 9/1998 | Bruce ............... 604/523 |
| 5,895,374 A | 4/1999 | Rodsten |
| 6,053,905 A | 4/2000 | Daignault et al. |
| 6,059,107 A | 5/2000 | Nosted et al. |
| 6,090,075 A | 7/2000 | House |
| 6,176,849 B1 | 1/2001 | Yang et al. |
| 6,217,569 B1 | 4/2001 | Fiore |
| 6,402,736 B1 * | 6/2002 | Brown et al. ............... 604/523 |
| 6,409,717 B1 | 6/2002 | Israelsson et al. |
| 6,471,684 B2 | 10/2002 | Dulak et al. |
| 6,527,748 B1 * | 3/2003 | Suzuki ............... 604/171 |
| 6,578,709 B1 | 6/2003 | Kavanagh et al. |
| 6,602,244 B2 | 8/2003 | Kavanagh et al. |
| 6,632,204 B2 * | 10/2003 | Guldfeldt et al. ............... 604/349 |
| 6,634,498 B2 | 10/2003 | Kayerod et al. |
| 6,673,053 B2 | 1/2004 | Wang et al. |
| 6,736,805 B2 | 5/2004 | Israelsson et al. |
| 6,790,220 B2 * | 9/2004 | Morris et al. ............... 606/213 |
| 6,848,574 B1 | 2/2005 | Israelsson et al. |
| 6,936,222 B2 * | 8/2005 | Mortensen et al. ............... 422/45 |
| 6,976,950 B2 * | 12/2005 | Connors et al. ............... 600/29 |
| 7,025,755 B2 * | 4/2006 | Epstein ............... 604/500 |
| 7,048,719 B1 * | 5/2006 | Monetti ............... 604/171 |
| 7,207,950 B2 * | 4/2007 | Goldenberg ............... 600/562 |
| 7,226,423 B2 * | 6/2007 | Goldenberg ............... 600/562 |
| 2001/0001443 A1 | 5/2001 | Kayerod et al. |
| 2001/0007060 A1 | 7/2001 | Fiore |
| 2001/0027295 A1 | 10/2001 | Dulak et al. |
| 2001/0027299 A1 | 10/2001 | Yang et al. |
| 2002/0177804 A1 * | 11/2002 | Saab ............... 604/45 |
| 2003/0018302 A1 | 1/2003 | Kavanagh et al. |
| 2003/0187367 A1 * | 10/2003 | Odland ............... 600/573 |
| 2003/0229264 A1 * | 12/2003 | Connors et al. ............... 600/29 |
| 2003/0236442 A1 * | 12/2003 | Connors et al. ............... 600/29 |
| 2004/0059298 A1 * | 3/2004 | Sanderson ............... 604/171 |
| 2004/0074794 A1 | 4/2004 | Conway et al. |
| 2004/0077998 A1 * | 4/2004 | Morris ............... 604/93.01 |
| 2004/0087921 A1 | 5/2004 | Guldfeldt et al. |
| 2004/0153051 A1 | 8/2004 | Israelsson et al. |
| 2004/0256264 A1 | 12/2004 | Israelsson et al. |
| 2004/0260245 A1 * | 12/2004 | Clem et al. ............... 604/171 |
| 2005/0015076 A1 | 1/2005 | Giebmeyer et al. |
| 2005/0070882 A1 * | 3/2005 | McBride ............... 604/544 |
| 2005/0109648 A1 | 5/2005 | Kerzman et al. |
| 2005/0137582 A1 | 6/2005 | Kull-Osterlin et al. |
| 2005/0187427 A1 * | 8/2005 | Connors et al. ............... 600/29 |
| 2005/0197531 A1 * | 9/2005 | Cabiri et al. ............... 600/116 |
| 2005/0288652 A1 * | 12/2005 | Suzuki ............... 604/516 |
| 2006/0025753 A1 * | 2/2006 | Kubalak et al. ............... 604/544 |
| 2006/0229566 A1 * | 10/2006 | Hanagasaki ............... 604/171 |

* cited by examiner

US 8,888,747 B2

CATHETER ASSEMBLY WITH VENTS

BACKGROUND OF THE INVENTION

1. Field of the Invention

The present invention relates generally to catheter assemblies. More particularly, the present invention relates to catheter assemblies having vents.

2. Background of the Invention

The urinary catheterization procedure is a common medical practice with the procedure being performed today in both hospital and home settings. In the hospital setting, nurses often perform catheterization procedures using convenience packs, or pre-assembled kits, which typically contain a vinyl or red latex rubber catheter, a waterproof absorbent underpad, a fenestrated drape, disposable gloves, a sealed packet containing about 22.5 mL of Povidone-Iodine solution, several prepping cotton balls in a disposable tray compartment, a sealed packet containing sterile lubricating jelly, a plastic forceps, a sterile specimen bottle, and a 1000 mL graduated basin. All of these items are packaged together and sterilized. To perform the catheterization procedure, a nurse opens the tray, dons sterile gloves and places the drape around the patient's genitalia. The Povidone-Iodine packet is opened and poured over the cotton balls. The packet of lubricating jelly is then opened and squeezed onto a sterile field. The patient's urethral opening is cleansed with the saturated cotton balls, holding each cotton ball with the forceps. Then, the nurse runs the tip end of the catheter, comprising the first inch or two (about 2.5 cm to about 5 cm) of the insertable portion, through the lubricating jelly. The catheter is then inserted into the patient's urethra and advanced until urine begins to flow through the catheter. The urine is drained into the receptacle and a urine specimen is caught in the collection if needed. The catheter is then removed and all the aforementioned items are discarded. Care must be taken to maintain sterile procedure in order to reduce the risk of urinary tract infection.

Because multiple steps are involved in the catheterization procedure and the slippery, lubricated catheter is not easily manipulated into the patient's urethra, a nurse typically spends a significant amount of time (e.g., 10-15 minutes) carrying out each catheterization. This basic procedure is used in virtually every inpatient hospital around the world, and has remained essentially the same for 50 years. This same procedure is employed out of the hospital setting as well.

As a result of the complications associated with the current catheterization process as described above, there are current techniques that utilize a closed sheath or protective covering in order to maintain the sterility of the catheter. However, in all of these closed sheathed designs, the operator has difficulty fully inserting the catheter into the patient's urethra as a result of an increase in air pressure within the protective sheath. This buildup of air pressure within the closed protective sheath arises when the operator guides the catheter into the patient's urethra. Thus, it becomes difficult to guide the remainder of the catheter into the patient's urethra because air pockets inhibit the progress of the catheter. Thus, there is a need for a catheter assembly with a closed protective sheath that is not subject to this and related problems.

SUMMARY OF THE INVENTION

The present invention provides a solution to an increased in air pressure within catheter assemblies having a closed protective sheath. In these catheter assemblies, a build up of air within the closed protective sheathes makes it difficult for the operator to fully advance the catheter into the patient's urethra. In order to solve this problem, the present invention discloses the utilization of vents in the form of small openings at the distal (or alternatively, proximal) portion of the catheter assembly in order to allow trapped air to escape freely to the external environment. In this way, the operator will not experience the resistance encountered with air buildup within the protective sheath. By placing the vents at the distal portion of the catheter assembly, any potential contamination may be isolated from the portion of the catheter actually entering the body. The present invention further minimizes contamination from the external environment by disclosing various techniques for opening the vents just prior to catheter assembly use or during catheter insertion.

In one exemplary embodiment of the present invention, a catheterization device is disclosed that includes a closed protective sheath with vents in the form of small openings. These small openings may be located at the distal portion of the catheterization device and may optionally be covered by removable seals. The removable seals can individually seal each small opening or a larger seal such as a tab or bag can be used to seal many small openings. The latter would provide for a decreased cost of manufacturing if a large number of small openings were employed. The operator can remove these seals via a seal tab immediately prior to catheter insertion or during catheter insertion as needed to minimize external contamination.

In another exemplary embodiment, the small openings may be formed from a valve attached to the protective sheath that connects the inside of the protective sheath with the external environment. In this embodiment, the valve may optionally be covered by a removable seal or an attached plug that can easily be removed immediately prior to catheter insertion or during catheter insertion as needed. The valve may avoid the intricacies and higher cost of manufacturing involved in cutting the openings into the protective sheath itself.

In another exemplary embodiment, the small openings in the catheterization device may be formed from a gas permeable membrane or a slitted membrane forming several, for example four, flaps. In this way, the operator does not have to manually engage the ventilation system. In yet another exemplary embodiment, the small openings may be situated on a distal terminus body attached to the protective sheath. These small openings may connect the interior of the protective sheath with the external environment and may also be covered with seals to minimize external contamination.

In the following descriptions of the present invention, "proximal" is used to refer to the portion of the catheter assembly situated closer to the patient's urethra during catheter insertion while "distal" is used to refer to the portion of the catheter assembly situated farther from the patient's urethra during catheter insertion.

DETAILED DESCRIPTION OF THE INVENTION

The present invention includes techniques for preventing air buildup within a protective sheath during operation of catheter assemblies containing a closed or substantially closed sheath. The present invention makes it easier to manipulate a catheter assembly containing a closed sheath by providing vents at the distal (or alternatively, proximal) portion of the catheter assembly. These vents may allow gas exchange between the internal surface of the protective sheath and the external environment. Such a gas exchange may ameliorate the problem of a buildup of air pressure within the protective sheath during catheter insertion. Use of these vents at the distal portion of the catheter assemblies may minimize potential catheter contamination to an area of the catheter not inserted in the patient's urethra. Additionally, the present invention includes a technique for further minimizing contamination from external sources by providing a removable covering for the vents which may be engaged just prior to catheter use, or during catheter insertion when resistance to catheter guidance is experienced.

Figure 1:
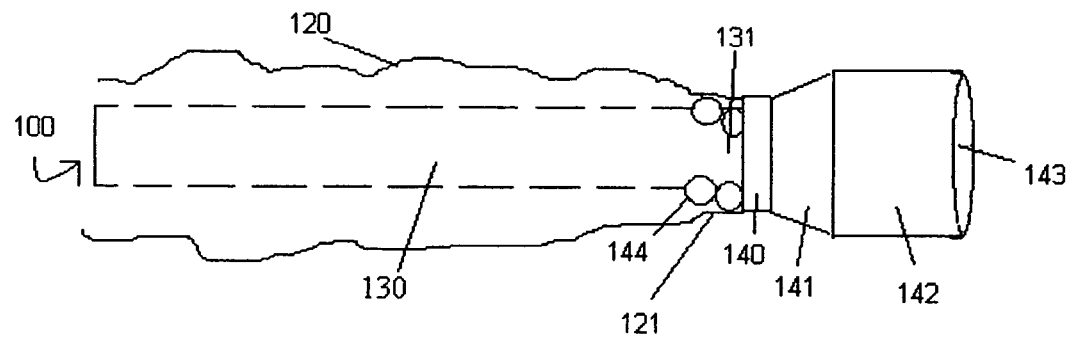
FIG. 1 shows a side view of a catheter assembly with openings located at a distal portion of the catheter assembly according to an exemplary embodiment of the present invention.

An exemplary embodiment of the present invention is catheter assembly 100 shown in FIG. 1, and includes a protective sheath 120, a catheter 130, a seal 140, a distal connector 141, a distal end 142, a urine outlet 143, and small openings 144. The protective sheath 120 may maintain catheter sterility and also provides a gripping surface for the operator. The protective sheath 120 may optionally contain a lubricating compound such as a hydrogel or aqueous solution to ease the movement of the catheter 130 through the protective sheath 140. The sheath itself can be composed of gas and liquid impermeable biocompatible materials such as, but not limited to, polyester based biocompatible polymers, nylon-based biocompatible polymers, latex based biocompatible polymers, Teflon, polytetrafluoroethylene (PTFE) polymers, polyvinyl chloride (PVC) polymers, silicone polymers, polyurethane polymers, silicone polyurethane polymers, ethylene-vinyl acetate copolymers, polyethylene polymers, and thermoplastic polymers. The distal sheath terminus 121 may be fastened to the distal connecter 141 via seal 140 so that a contamination-free seal is produced. The method used to create the seal 140 includes but is not limited to heat shrinking, but may be any other appropriate technique suitable for the purpose of seal 140 as described, as apparent to one having ordinary skill in the art.

The distal end 131 of catheter 130 may reside just proximal to the seal 140 or it may be flush with the seal 140. Thus, the distal end 131 may be proximal to the distal connector 141 as shown in FIG. 1. The small openings 144 may function as vents for the catheter assembly and are situated on the distal sheath terminus 121 just proximal to the seal 140. The small openings 144 are depicted in FIG. 1 as being circular. However, they can be of any design including but not limited to other geometric shapes (e.g., diamonds, rectangles, triangles, and other polygons), vertical slits, horizontal slits, and crosses, provided that the small openings 144 retain the function of allowing gas exchange between the inside of the distal sheath terminus 121 and the external environment while minimizing the sheath area exposed to potential external contamination. Although the small openings 144 are depicted as being quite large in FIG. 1, they can be of any diameter as long as they efficiently allow gas exchange while minimizing the area of the distal sheath terminus 121 exposed to the external environment. In this way, the small openings 144 may allow an efficient gas exchange between the inside of the distal sheath terminus 121 while maintaining a relatively sterile internal environment for the catheter 130 at the distal sheath terminus 121.

During catheter insertion, the user should avoid or minimize contact with the small openings 144 at the distal sheath terminus 121 in order to better ensure catheter sterility, and allow for better gas exchange. This should not be a problem since most of the manipulation of closed sheath catheter assemblies is performed at the proximal end during catheter insertion. As the protective sheath 120 is manipulated toward the distal end of the catheter assembly during use, the small openings 144 may provide a technique for fluid communication with the inside of the sheath and the external environment. Thus, as the air pressure increases within the protective sheath 120 during catheter insertion, the small openings 144 may allow trapped air to escape thereby allowing a smoother, easier catheter insertion.

Figure 2:
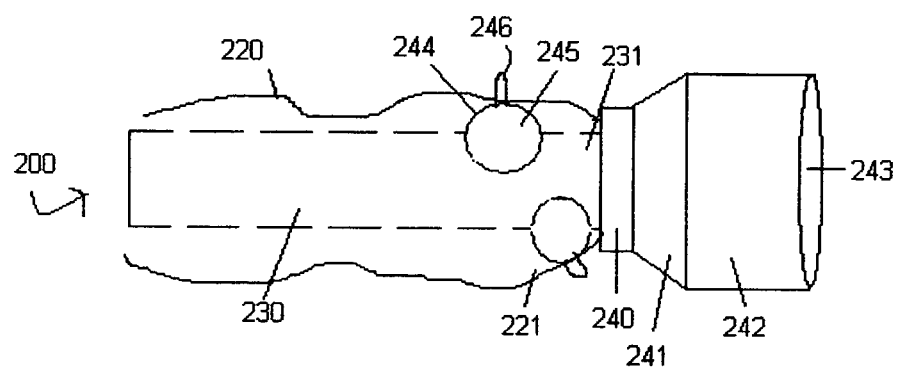
FIG. 2 shows a side view of a catheter assembly with openings covered by removable seals according to an exemplary embodiment of the present invention.

Another exemplary embodiment of the present invention is catheter assembly 200 shown in FIG. 2, and includes a protective sheath 220, a catheter 230, a seal 240, a distal connector 241, a distal end 242, a urine outlet 243, small openings 244, removable seals 245, and seal tabs 246. In this exemplary embodiment, the protective sheath 220 may maintain catheter sterility and also provide a grip for the operator during catheterization. The distal sheath terminus 221 may be fastened to the distal connecter 241 via seal 240 so that a contamination-free seal is produced. The technique used to create the seal 240 includes, but is not limited to, heat shrinking or any other appropriate method suitable for the purpose of seal 240 as described.

The distal end 231 of catheter 230 may reside just proximal to the seal 240 or it may be flush with the seal 240. Thus, the distal end 231 may be proximal to the distal connector 241 as shown in FIG. 2. The small openings 244 may function as vents to allow gas transfer between the inside of protective sheath 220 and the external environment. The small openings 244 may be situated at the distal portion of the protective sheath 220 in order to isolate any potential contamination to the distal, uninserted portion of the catheter 230. This exemplary embodiment may include removable seals 245 with seal tabs 246. The removable seals 245 can be composed of any material that can bind via an adhesive to the protective sheath 220 weakly enough to be pulled off but strongly enough to resist falling off the protective sheath 220 prematurely (e.g., using aluminum foil or silicone). The removable seals 245 may enable the operator to expose the small openings 244 just prior to catheter insertion or during catheter insertion as needed. In this way, the distal portion of catheter 230 may be exposed to the external environment for only a short period of time thereby minimizing potential contamination. To engage the removable seals 245, the operator may grasp the seal tabs 246 attached to the surface of the removable seals 245 and may pull the removable seals 245 off of the small openings 244. In this manner, the operator is able to relieve the air pressure produced within the protective sheath 220 by allowing the trapped air to escape through the small openings 244.

The small openings 244 are depicted in FIG. 2 as being circular. However, they can be of any design including but not limited to other geometric shapes (e.g., diamonds, rectangles, triangles, and other polygons), vertical slits, horizontal slits, and crosses provided that the small openings 244 retain the function of allowing gas exchange between the inside of the distal sheath terminus 221 and the external environment while minimizing the sheath area exposed to potential external contamination. Although the small openings 244 are depicted as being relatively large in FIG. 2, they can be of any diameter as long as they efficiently allow the said gas exchange while minimizing the area of the distal sheath terminus 221 exposed to the external environment. In this way, the small openings 244 allow an efficient gas exchange between the inside of the distal sheath terminus 221 while maintaining a relatively sterile internal environment for the catheter 230 at the distal sheath terminus 221.

Figure 3:
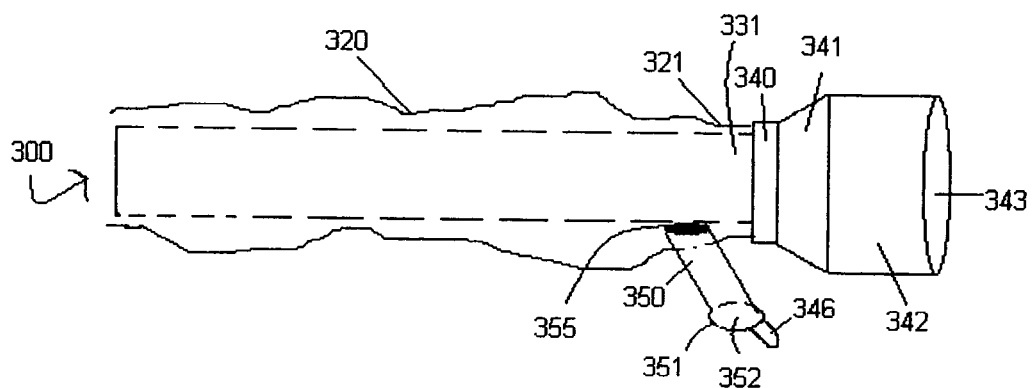
FIG. 3 shows a side view of a catheter assembly with an opening formed from a valve with a removable seal with the valve connecting the inside of the protective sheath with the external environment according to an exemplary embodiment of the present invention.

Yet another exemplary embodiment of the present invention is catheter assembly 300 shown in FIG. 3, and includes a protective sheath 320, a catheter 330, a seal 340, a distal connector 341, a distal end 342, a urine outlet 343, an attachment point 355, a valve 350, an aperture 351, a removable aperture seal 352, and a seal tab 346. In this exemplary embodiment, the protective sheath 320 may maintain catheter sterility and also provide a grip for the operator during catheterization. The distal sheath terminus 321 may be fastened to the distal connecter 341 via seal 340 so that a contamination-free seal is produced. The technique used to create the seal 340 includes, but is not limited to, heat shrinking or any other appropriate method suitable for the purpose of seal 340 as described.

The distal end 331 of catheter 330 may reside just proximal to the seal 340 or it may be flush with the seal 340. Thus, the distal end 331 may be proximal to the distal connector 341 as shown in FIG. 3. The attachment point 355 may be located on the distal sheath terminus 321. Attachment point 355 may serve to anchor and connect the valve 350 to the protective sheath 320 and can be formed using a variety of adhesive techniques including, but not limited to, any form of welding. Attachment point 355 may also be part of a separate component, such as a collar, with valve 350 coming through the sheath 320. The valve 350 is depicted as a cylinder in FIG. 3 but can be of various geometric designs.

The valve 350 may be an extension off of the protective sheath 320 and may be in fluid communication with the inside of protective sheath 320. Thus, the valve 350 may be open on both of its ends with an opening in between allowing gas passage. The valve 350 may have a removable aperture seal 352 covering aperture 351 on the end opposite the attachment point 355. The removable aperture seal 352 may have attached to its surface a seal tab 346. The removable seals 352 can be composed of any material that can bind via adhesive to the valve 350 weakly enough to be pulled off but strongly enough to resist falling off prematurely (e.g., aluminum foil or silicone). The seal tab 346 may be grasped by the operator to pull off the removable aperture seal 352 just prior to catheter insertion or during catheter insertion. In this way, any air buildup within the protective sheath 320 may be relieved by exposing the aperture 351 of the valve 350 to the external environment for a short period of time. Gas may thus be allowed to pass from inside of the protective sheath 320 to the external environment through the throughbore of the valve 350. The valve 350 can be of any suitable diameter in order to allow an effective volume of air to escape from the protective sheath 320 while at the same time minimizing the potential for external contamination to invade the catheter assembly.

Alternatively, the aperture seal 352 can be puncturable and thus would be pierced by the operator in order to expose the aperture 351 to the external environment. This puncturable seal could be composed of, but is not limited to, silicone or aluminum foil material as mentioned above. In another variation of the exemplary embodiment shown in FIG. 3, the end portion of valve 350 could be sealed with a slitted center section instead of aperture 351 as previously discussed. For example, the end portion of valve 350 could include a crossed slitted covering forming multiple, for example four, flaps. The flaps of this design may be composed of the same material used for the valve 350 and/or the protective sheath 320 (e.g., any non-biodegradable polymer). In this way, contamination could still be minimized while the operator would not have to exert energy removing any seals. Also in this design, the operator could manipulate the amount of gas passing through the valve 350 by squeezing the crossed slitted covering thereby increasing the space for gas to escape as needed.

Figure 4:
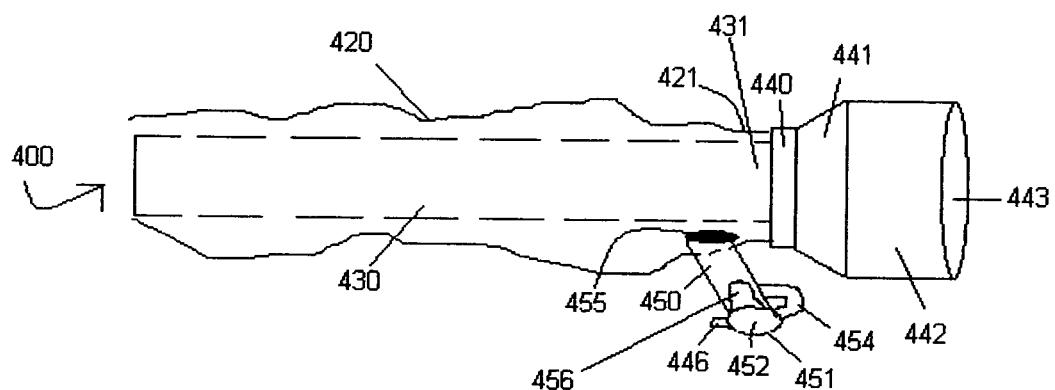
FIG. 4 shows a side view of a catheter assembly with an opening formed from a valve with a removable plug with the valve connecting the inside of the protective sheath with the external environment according to an exemplary embodiment of the present invention.

Another exemplary embodiment of the present invention is catheter assembly 400 shown in FIG. 4, and includes a protective sheath 420, a catheter 430, a seal 440, a distal connector 441, a distal end 442, a urine outlet 443, an attachment point 455, a valve 450, an aperture 451, a removable aperture seal 452, a seal tab 446, a connector arm 454, and a plug 456. The protective sheath 420 may maintain catheter sterility and also provides a grip for the operator during catheterization. The distal sheath terminus 421 may be fastened to the distal connecter 441 via seal 440 so that a contamination-free seal is produced. The technique used to create the seal 440 includes, but is not limited to, heat shrinking or any other appropriate method suitable for the purpose of seal 440 as described.

The distal end 431 of catheter 430 may reside just proximal to the seal 440 or it may be flush with the seal 440. Thus, the distal end 431 may be proximal to the distal connector 441 as shown in FIG. 4. The attachment point 455 may be located on the distal sheath terminus 421. Attachment point 455 may serve to anchor and connect the valve 450 to the protective sheath 420 and can be formed using a variety of adhesive techniques including but not limited to any form of welding. Attachment point 455 may also be part of a separate component, such as a collar, with valve 450 coming through the sheath 420. The valve 450 is depicted as a cylinder in FIG. 4 but can be of various geometric designs. The valve 450 may be an extension off of the protective sheath 420 and may be in fluid communication with the inside of protective sheath 420. Thus, the valve 450 may be open on both of its ends with an opening in between allowing gas passage. The valve 450 may have a removable aperture seal 452 covering aperture 451 on the end opposite the attachment point 455. The removable aperture seal 452 may have attached to its inner surface a plug 456 and to its outer surface a seal tab 446. The removable aperture seal 452 may be connected to the body of the valve 450 via a connector arm 454. The seal tab 446 may be grasped by the operator to pull off the removable aperture seal 452 with plug 456 just prior to catheter insertion or during catheter insertion. In this way, any air buildup within the protective sheath 420 may be relieved by exposing the aperture 451 of the valve 450 to the external environment for a short period of time. Gas may thus be allowed to pass from inside of the protective sheath 420 to the external environment through the opening of the valve 450. The valve 450 can be of any suitable diameter in order to allow an effective volume of air to escape from the protective sheath 420 while at the same time minimizing the potential for external contamination to invade the catheter assembly. In this exemplary embodiment, the aperture seal 452 and plug 456 may remain connected to the valve 450 via connecter arm 454 after removal and therefore can be reinserted if necessary.

Figure 5:
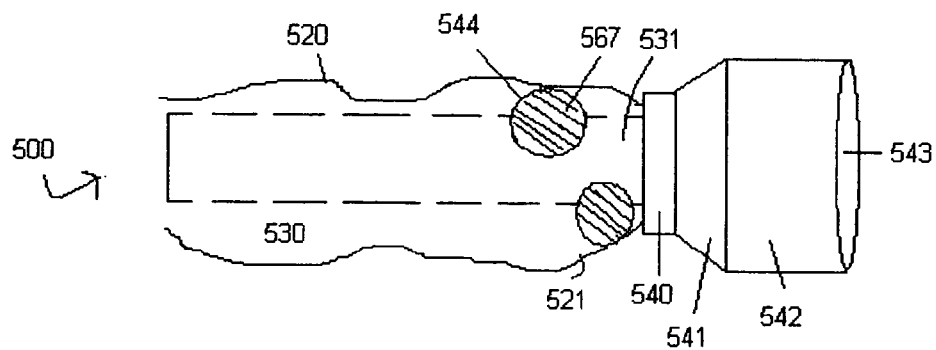
FIG. 5 shows a side view of a catheter assembly with openings formed from a gas permeable membrane according to an exemplary embodiment of the present invention.

Still another embodiment of the present invention is catheter assembly 500 shown in FIG. 5, and includes a protective sheath 520, a catheter 530, a seal 540, a distal connector 541, a distal end 542, a urine outlet 543, small openings 544, and gas permeable membranes 567. The gas permeable membranes 567 may cover the small openings 544 completely and may be flush with the surface of the protective sheath 520 or raised from the surface of the protective sheath 520. The gas permeable membranes 567 may function as vents to allow trapped gas to escape from the inside of the protective sheath 520 to the external environment.

These membranes can be composed of any permeable material that may allow the passage of air but may be dense enough to prevent or minimize the passage of gel or liquid. Thus, the gas permeable membranes 567 may be permeable to at least $O_2$ and $N_2$ since air is composed of roughly 99% of these gases. The membranes may be composed of materials with the selective permeability which include, but not be limited to, polyimide copolymers. In this exemplary embodiment, the protective sheath 520 may maintain catheter sterility and also provides a grip for the operator during catheterization. The distal sheath terminus 521 may be fastened to the distal connecter 541 via seal 540 so that a contamination-free seal is produced. The technique used to create the seal 540 includes, but is not limited to, heat shrinking or any other appropriate method suitable for the purpose of seal 540 as described. The distal end 531 of catheter 530 may reside just proximal to the seal 540 or it may be flush with the seal 540. Thus, the distal end 531 may be proximal to the distal connector 541 as shown in FIG. 5.

Figure 6:
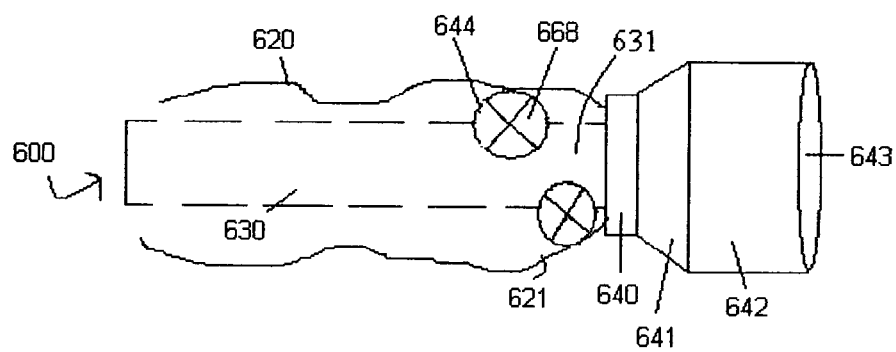
FIG. 6 shows a side view of a catheter assembly with openings formed from a slitted membrane forming a multi flap design according to an exemplary embodiment of the present invention.

Another exemplary embodiment of the present invention is catheter assembly 600 shown in FIG. 6, and includes a protective sheath 620, a catheter 630, a seal 640, a distal connector 641, a distal end 642, a urine outlet 643, small openings 644, and slitted membranes 668. The slitted membranes can be situated flush to the surface of the protective sheath 620 at the small openings 644 or they can be raised from the surface of the protective sheath 620 at the small openings 644. The membranes may be composed of any non-biodegradable polymer similar to the rest of the materials for all of the exemplary embodiments disclosed. The cuts in the slitted membranes 668 may be made by any uniformly sharp and sterile object. Alternatively, the membranes could be cut with only a single slit thus not producing the multiple flapped design as illustrated in FIG. 6.

The protective sheath 620 may maintain catheter sterility and also provides a grip for the operator during catheterization. The distal sheath terminus 621 may be fastened to the distal connecter 641 via seal 640 so that a contamination-free seal is produced. The method used to create the seal 640 includes, but is not limited to, heat shrinking or any other appropriate method suitable for the purpose of seal 640 as described. The distal end 631 of catheter 630 may reside just proximal to the seal 640 or it may be flush with the seal 640. Thus, the distal end 631 may be proximal to the distal connector 641 as shown in FIG. 6.

Figure 7:
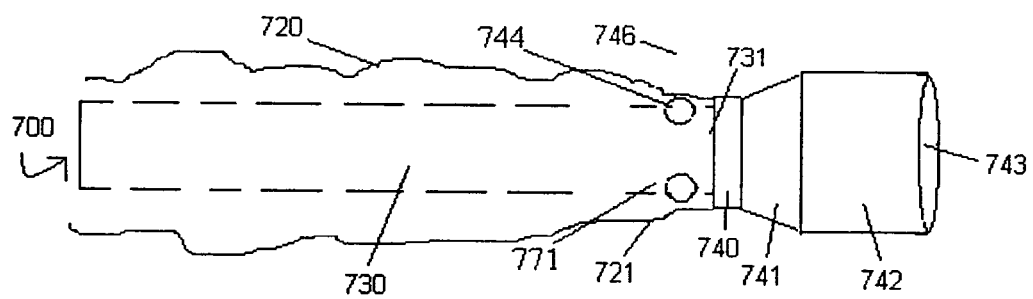
FIG. 7 shows a side view of a catheter assembly with openings covered by a removable strip according to an exemplary embodiment of the present invention.

Yet another exemplary embodiment of the present invention is catheter assembly 700 shown in FIG. 7, and includes a protective sheath 720, a catheter 730, a seal 740, a distal connector 741, a distal end 742, a urine outlet 743, small openings 744, a removable band 771, and a seal tab 746. The protective sheath 720 may maintain catheter sterility and may also provide a grip for the operator during catheterization. The distal sheath terminus 721 may be fastened to the distal connecter 741 via seal 740 so that a contamination-free seal is produced. The technique used to create the seal 740 includes, but is not limited to, heat shrinking or any other appropriate method suitable for the purpose of seal 740 as described.

The distal end 731 of catheter 730 may reside just proximal to the seal 740 or it may be flush with the seal 740. Thus, the distal end 731 may be proximal to the distal connector 741 as shown in FIG. 7. The small openings 744 may function as vents to allow gas transfer between the inside of protective sheath 720 and the external environment. The small openings 744 may be situated at the distal portion of the protective sheath 720 in order to isolate any potential contamination to the distal, uninserted portion of the catheter 730. This exemplary embodiment may include a removable band 771 that covers the small openings 744 until it is necessary to expose the small openings 744 to the external environment. The removable band 771 can be composed of any material that can bind via an adhesive to the protective sheath 720 weakly enough to be pulled off but strongly enough to resist falling off the protective sheath 720 prematurely (e.g., aluminum foil or silicone). The removable band 771 can wrap all the way around the distal sheath terminus 721 forming a circular band or the removable band 771 can cover only a portion of the diameter of the distal sheath terminus 721. The removable band 771 may enable the operator to expose the small openings 744 just prior to catheter insertion or during catheter insertion as needed. In this way, the distal portion of catheter 730 may be exposed to the external environment for only a short period of time thereby minimizing potential contamination. To engage the removable band 771, the operator may grasp the seal tab 746 attached to the surface of the removable band 771 and may pull the removable band 771 off of the small openings 744. In this manner, the operator may be able to relieve the air pressure produced within the protective sheath 720 by allowing the trapped air to escape through the small openings 744.

The small openings 744 are depicted in FIG. 7 as being circular. However, they can be of any design including, but not limited to, other geometric shapes (e.g., diamonds, rectangles, triangles, and other polygons), vertical slits, horizontal slits, and crosses provided that the small openings 744 retain the function of allowing gas exchange between the inside of the distal sheath terminus 721 and the external environment while minimizing the sheath area exposed to potential external contamination. Although the small openings 744 are depicted as being quite large in FIG. 7, they can be of any diameter as long as they efficiently allow the said gas exchange while minimizing the area of the distal sheath terminus 721 exposed to the external environment. In this way, the small openings 744 may allow an efficient gas exchange between the inside of the distal sheath terminus 721 while maintaining a relatively sterile internal environment for the catheter 730 at the distal sheath terminus 721.

Figure 8:
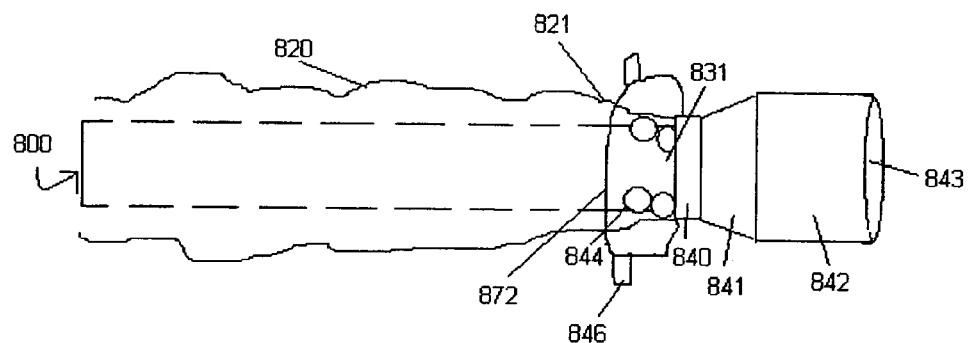
FIG. 8 shows a side view of a catheter assembly with openings covered by a removable bag of a larger diameter than the protective sheath according to an exemplary embodiment of the present invention.

Yet another exemplary embodiment of the present invention is catheter assembly 800 shown in FIG. 8, and includes a protective sheath 820, a catheter 830, a seal 840, a distal connector 841, a distal end 842, a urine outlet 843, small openings 844, a removable bag 872, and seal tab 846. The protective sheath 820 may maintain catheter sterility and may also provide a grip for the operator during catheterization. The distal sheath terminus 821 may be fastened to the distal connecter 841 via seal 840 so that a contamination-free seal is produced. The technique used to create the seal 840 includes, but is not limited to, heat shrinking or any other appropriate method suitable for the purpose of seal 840 as described.

The distal end 831 of catheter 830 may reside just proximal to the seal 840 or it may be flush with the seal 840. Thus, the distal end 831 may be proximal to the distal connector 841 as shown in FIG. 8. The small openings 844 may function as vents to allow gas transfer between the inside of protective sheath 820 and the external environment. The small openings 844 may be situated at the distal portion of the protective sheath 820 in order to isolate any potential contamination to the distal, uninserted portion of the catheter 830. This exemplary embodiment may include a removable bag 872 that covers the small openings 844 until it is necessary to expose the small openings 844 to the external environment. The removable bag 872 can be composed of any material that can bind via an adhesive to the protective sheath 820 weakly enough to be pulled off but strongly enough to resist falling off the protective sheath 820 prematurely (e.g., aluminum foil or silicone). The removable bag 872 may be of a larger diameter than the diameter of the protective sheath 820 to make it easier to remove the bag as needed. The removable bag 872 can be peeled down the distal sheath terminus 821 thereby exposing the small openings 844 just prior to catheter insertion or during catheter insertion as needed. In this way, the distal portion of catheter 830 may be exposed to the external environment for only a short period of time thereby minimizing potential contamination. To engage the removable bag 872, the operator may grasp the seal tabs 846 attached to the surface of the removable bag 872 and may pull the removable bag 872 off of the small openings 844. In this manner, the operator may relieve the air pressure produced within the protective sheath 820 by allowing the trapped air to escape through the small openings 844.

The small openings 844 are depicted in FIG. 8 as being circular. However, they can be of any design including, but not limited to, other geometric shapes (e.g., diamonds, rectangles, triangles, and other polygons), vertical slits, horizontal slits, and crosses provided that the small openings 844 retain the function of allowing gas exchange between the inside of the distal sheath terminus 821 and the external environment while minimizing the sheath area exposed to potential external contamination. Although the small openings 844 are depicted as being quite large in FIG. 8, they can be of any diameter as long as they efficiently allow the said gas exchange while minimizing the area of the distal sheath terminus 821 exposed to the external environment. In this way, the small openings 844 may allow an efficient gas exchange between the inside of the distal sheath terminus 821 while maintaining a relatively sterile internal environment for the catheter 830 at the distal sheath terminus 821.

Figure 9A:
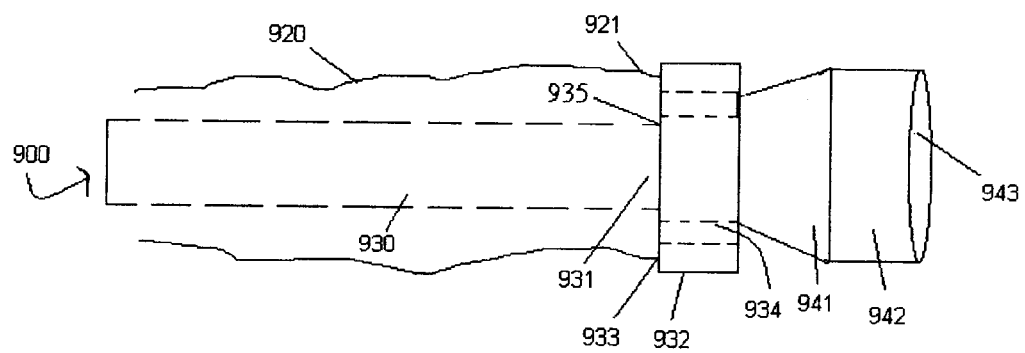
FIG. 9A shows a side view of a catheter assembly with openings in a distal terminus body connected to the protective sheath according to an exemplary embodiment of the present invention.

Another embodiment of the present invention is catheter assembly 900 shown in FIG. 9A, and includes a protective sheath 920, a catheter 930, a distal terminus body 932 with throughbores 934 and 935, a distal connector 941, a distal end 942, and a urine outlet 943. The protective sheath 920 may maintain catheter sterility and may also provide a grip for the operator during catheterization. The distal sheath terminus 921 may be fastened to the distal terminus body 932 at attachment point 933 so that a contamination-free seal is produced. The technique used to create the connection at attachment point 933 includes, but is not limited to, heat sealing or any other appropriate method suitable to obtain a contamination-free seal.

Figure 9B:
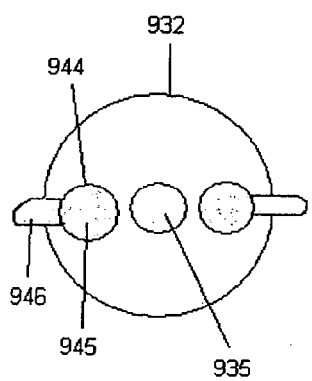
FIG. 9B shows an end view of the distal terminus body connected to the protective sheath with removable seals according to an exemplary embodiment of the present invention.
Figure 9C:
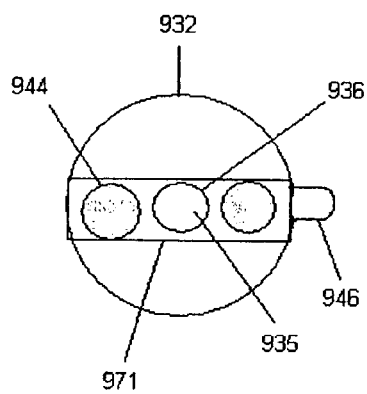
FIG. 9C shows another end view of the distal terminus body connected to the protective sheath with a removable strip according to an exemplary embodiment of the present invention.

The distal end 931 of catheter 930 may reside just proximal to the seal 940 or it may be flush with the seal 940. Thus, the distal end 931 may be proximal to the distal connector 941 as shown in FIG. 9A. The throughbores 934 in the distal terminus body 932 may be in fluid communication with the inside of the protective sheath 920. The throughbore 935 may be of a slightly larger diameter than the catheter 930 and may allow the catheter to pass through into the distal connector 941. The ends of the throughbores 934 may be open on the proximal side of the distal terminus body 932 while the ends of the throughbores 934 on the distal side of the distal terminus body 932 may be open as well but may be initially covered as shown in FIG. 9B and FIG. 9C. In this way, the operator can expose the small openings 944 to the external environment just prior to catheter insertion or during catheter insertion as needed in order to relieve built up air pressure within the protective sheath 920. The operator may grasp the seal tabs 946 in both of the exemplary embodiments shown in FIG. 9B and FIG. 9C and remove either the removable seals 945 or the removable band 971 to expose the openings. If the removable band 971 is used, then it could contain a circular aperture 936 of the same diameter as throughbore 935 of the distal terminus body 932 to allow the catheter to pass through to the distal connector 941.

The removable band 971 and the removable seals 945 can be composed of any material that can bind via an adhesive to the distal terminus body 932 weakly enough to be pulled off but strongly enough to resist falling off the distal terminus body 932 prematurely (e.g. aluminum foil or silicone).

The small openings 944 are depicted in FIG. 9B and FIG. 9C as being circular. However, they can be of any design including but not limited to other geometric shapes (e.g., diamonds, rectangles, triangles, and other polygons), vertical slits, horizontal slits, and crosses provided that the small openings 944 retain the function of allowing gas exchange between the inside of the distal sheath terminus 921 and the external environment while minimizing the sheath area exposed to potential external contamination. Although the small openings 944 are depicted as being quite large in FIG. 9B and FIG. 9C, they can be of any diameter as long as they efficiently allow the said gas exchange while minimizing the area of the distal sheath terminus 921 exposed to the external environment. In this way, the small openings 944 may allow an efficient gas exchange between the inside of the distal sheath terminus 921 while maintaining a relatively sterile internal environment for the catheter 930 at the distal sheath terminus 921.

In this disclosure, wherein the exact material is not specified for the component part, any biocompatible polymer such as a polyester based biocompatible polymer, nylon-based biocompatible polymer, latex based biocompatible polymer, Teflon, polytetrafluoroethylene (PTFE) polymer, polyvinyl chloride (PVC) polymer, silicone polymer, polyurethane polymer, silicone polyurethane polymer, ethylene-vinyl acetate copolymer, polyethylene polymer, and a thermoplastic polymer can be used. The methods used to manufacture the component parts as disclosed herein can be any method regularly used in the art and known to a person skilled in the art which are suitable for the purposes of the component parts as disclosed.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A urinary catheterization device, the device comprising:
   a urinary catheter;
   a protective sheath enclosing the urinary catheter;
   a lubricating compound coating the urinary catheter, the lubricating compound enclosed within the protective sheath; and
   an opening in the sheath which allows the exchange of gas between inside of the sheath and an external environment directly outside of the sheath such that gas escapes the sheath through the opening when the sheath is retracted as the urinary catheter is advanced into a patient's urethra;
   wherein the opening is covered by a seal comprising a layer that is easily puncturable, the layer comprising one of a silicone or a foil material.

2. The catheterization device of claim 1, wherein the opening is located on a distal portion of the protective sheath.

3. The catheterization device of claim 1, wherein the opening is located on a distal terminus body attached to the protective sheath.

4. The catheterization device of claim 1, wherein the opening is covered by a removable seal.

5. The catheterization device of claim 4, wherein the removable seal is of a circular shape.

6. The catheterization device of claim 1, wherein the opening is of a circular shape.

7. The catheterization device of claim 1, wherein a single removable seal covers one or more openings and is rectangular in shape.

8. The catheterization device of claim 1, wherein a single removable bag of a larger diameter than the protective sheath covers one or more openings.

9. The catheterization device of claim 1, wherein the opening is formed from an attached valve that connects the inside of the protective sheath with the external environment.

10. The catheterization device of claim 1, wherein the opening is slitted forming multiple flaps.

11. The catheterization device of claim 1, wherein the opening is formed from a gas permeable membrane.

12. A urinary catheterization device, the device comprising:
    a flexible urinary catheter;
    a protective sheath enclosing the urinary catheter at the proximal and distal ends of the urinary catheter;
    a lubricating compound coating the urinary catheter, the lubricating compound enclosed within the protective sheath; and
    openings in the sheath positioned nearby a distal portion of the urinary catheter which allow the exchange of gas between inside of the protective sheath and an external environment directly outside of the sheath such that gas escapes the sheath through the openings when the sheath is retracted as the urinary catheter is advanced into a patient's urethra;
    wherein the openings are covered by a seal comprising a layer that is easily puncturable, the layer comprising one of a silicone or a foil material.

13. The urinary catheterization device of claim 12, wherein the openings are covered by removable seals.

14. The urinary catheterization device of claim 13, wherein the removable seals are circular in shape.

15. The urinary catheterization device of claim 12, wherein the openings are circular in shape.

16. The urinary catheterization device of claim 12, wherein the openings are covered by a single removable seal that is rectangular in shape.

17. The catheterization device of claim 12, wherein the openings are covered by a single removable bag of a larger diameter than the protective sheath.

18. The catheterization device of claim 12, wherein the openings are formed from an attached valve that connects the inside of the protective sheath to the external environment.

19. The catheterization device of claim 12, wherein the openings are slitted with multiple flaps.

20. A urinary catheterization device, the device comprising:
    a flexible urinary catheter;
    a protective sheath containing a lubricating compound and enclosing the urinary catheter at proximal and distal ends of the urinary catheter;
    a lubricating compound coating the urinary catheter, the lubricating compound enclosed within the protective sheath; and
    openings in the sheath positioned nearby a distal portion of the urinary catheter which allow the exchange of gas between inside of the protective sheath and an external environment directly outside of the sheath such that gas escapes the sheath through the openings when the sheath is retracted as the urinary catheter is advanced into a patient's urethra;
    wherein the openings are covered by a seal comprising a layer that is easily puncturable, the layer comprising one of a silicone or a foil material.

* * * * *